United States Patent
Wong et al.

(10) Patent No.: US 6,805,856 B2
(45) Date of Patent: Oct. 19, 2004

(54) HAIR CARE COMPOSITIONS WHICH REDUCE COLOR LOSS IN HAIR AND METHODS OF USING THE COMPOSITIONS

(75) Inventors: Mike Wong, Plainsboro, NJ (US); Eva Memisha, Riverdale, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/123,208

(22) Filed: Apr. 17, 2002

(65) Prior Publication Data

US 2003/0198615 A1 Oct. 23, 2003

(51) Int. Cl.$^7$ .................................................. A61K 7/06
(52) U.S. Cl. ................................... 424/70.12; 424/70.1
(58) Field of Search .............................. 424/70.1, 70.12

(56) References Cited

U.S. PATENT DOCUMENTS 6,355,724 B1 * 3/2002 LeGrow et al. ............. 524/731

OTHER PUBLICATIONS

Marlanne D. Berthiaume, et al. "Effects of Silicon Pretreatment on Oxidative Hair Damage", Journal of the Society of Cosmetic Chemists, 46, 231–245, (Sep./Oct. 1995), pp. 231–242.

J. Jachowicz, et al., "Heterocoagulation of Silicon Emulsions on Keratin Fibers", Journal of Colloid and Interface Science, vol. 133, No. 1, Nov. 1989, pp. 118–134.

* cited by examiner

*Primary Examiner*—Jyothsna Venkat
(74) *Attorney, Agent, or Firm*—Oblon, Spivak, McClelland, Maier & Neustadt, P.C.

(57) ABSTRACT

The present invention provides hair care compositions comprising at least 10% of one or more polydialkylsiloxanes each having at least one pendant alkyl moiety, methods of using the compositions to reduce the loss of color in the hair, methods of using the compositions to reduce the effects of oxidation on the hair, and methods of using the compositions to add volume to the hair.

111 Claims, No Drawings

HAIR CARE COMPOSITIONS WHICH REDUCE COLOR LOSS IN HAIR AND METHODS OF USING THE COMPOSITIONS

FIELD OF THE INVENTION

The present invention provides hair care compositions which can be used to reduce color loss in hair, reduce the effects of oxidation of hair, and/or add volume to hair.

BACKGROUND OF THE INVENTION

Hair is composed of keratinous fibers and is inclusive of head hair, eyebrows, eyelashes, mustache, beard, and other types of body hair.

Human hair is also commonly dyed with various coloring agents. Such hair coloring agents often fade with time due to washing or upon exposure to ultraviolet radiation from the sun.

Therefore, there is a need for a class of hair treatment compositions that enable longer-lasting color retention on the hair.

In addition, ultraviolet light from the sun or other chemical treatments, reduce the hair's mechanical strength due to oxidation of the hair components and causes fading of natural and applied hair color. Therefore, there is also need for a novel class of hair treatment compositions which provide superior protection from oxidative effects of the sun that compromise hair structure.

SUMMARY OF THE INVENTION

The present invention addresses the problems set forth above. In one aspect, the present invention provides hair care compositions containing at least 10% by weight relative to the total weight of the composition of at least one polydialkylsiloxane having at least one pendant alkyl moiety.

In another aspect of the invention, methods for reducing the loss of color in hair are provided.

In a further aspect of the invention, methods for reducing the effects of oxidation on hair are provided.

In yet another aspect of the invention, methods for increasing the volume of hair are provided.

DETAILED DESCRIPTION OF THE INVENTION

In accordance with the present invention, hair care compositions comprising at least 10% by weight with respect to the total weight of the composition of at least one polydialkylsiloxane each having at least one pendant alkyl moiety, which polydialkylsiloxane has a vapor pressure of at least 0.8 mmHg, and preferably at least 2 mmHg at 25° C. are provided.

The compositions of the present invention comprise at least 10% of the polydialkylsiloxane including all ranges and subranges within this range such as, for example, at least 20%, at least 30%, at least 40%, least 50%, at least 60%, at least 70%, at least 80%, at least 90% and up to 100% by weight with respect to the total weight of the composition. The compositions may contain only one polydimethylsiloxane having at least one pendant alkyl moiety or they may comprise two or more (that is, at least two) the polydimethylsiloxanes.

When preparing the compositions of the present invention containing at least two of the polydimethylsiloxanes, the polydialkylsiloxanes can be provided simultaneously or can be added at different stages of production.

The pendant alkyl moiety is preferably a substituted or unsubstituted, branched or unbranched, alkane, alkene, alkyne, aryl chain, or a mixture thereof. The alkyl moiety can contain from about 1 carbon atom to about 50 carbon atoms, including from about 2 to about 30 carbon atoms and further including from about 3 to about 20 carbon atoms. Preferably, the alkyl moiety contains from about 4 to about 16 carbon atoms, and more preferably from about 5 to about 10 carbon atoms. In a preferred embodiment, the pendant alkyl moiety contains 6 carbon atoms.

When one of the pendant alkyl moieties is methyl, the polydialkylsiloxane can be an alkyl methicone. Thus, alkyl methicones having at least one pendant alkyl moiety as described above can be suitable polydialkylsiloxanes in accordance with the present invention. Preferably, the alkyl methicones are non-cyclic, linear methicones having a molecular weight of less than 1000 and are volatile at room temperature. Preferred alkyl methicones include, for example, butyl methicone, pentyl methicone, hexyl methicone, heptyl methicone, octyl methicone, nonyl methicone, decyl methicone, cetyl methicone, lauryl methicone, and stearyl methicone, with hexyl methicone being particularly preferred.

According to one aspect of the present invention, the polydialkylsiloxane having at least one pendant alkyl moiety has the following structure:

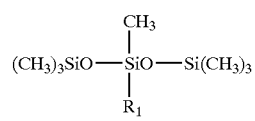

wherein $R_1$ is an alkyl moiety, which can be a substituted or unsubstituted, branched or unbranched, alkane, alkene, alkyne, aryl chain, or a mixture thereof. The alkyl moiety can contain from about 1 carbon atom to about 50 carbon atoms, including from about 2 to about 30 carbon atoms and further including from about 3 to about 20 carbon atoms. Preferably, the alkyl moiety contains from about 4 to about 16 carbon atoms, and more preferably from about 5 to about 10 carbon atoms. In a preferred embodiment, the alkyl moiety contains 6 carbon atoms.

According to another aspect of the present invention, the polydialkylsiloxane having at least one pendant alkyl moiety has the following structure:

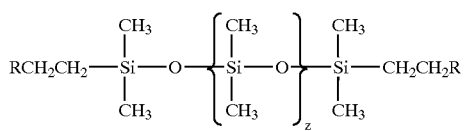

where R is hydrogen; or a branched or unbranched, substituted or unsubstituted alkyl group containing from about 1 to about 15 carbon atoms and z is from 1 to 5. The alkyl group can be an alkene, alkyne, or aryl group. In a preferred embodiment, R and z are selected such that the molecular weight of the compound is from about 300 to about 600. In another embodiment, the hydrocarbon-to-silicone ratio in the formula above is from about 0.25 to about 1.00.

According to one aspect of the present invention, the polydialkylsiloxanes described herein are evaporative polydialkylsiloxanes. One advantage of using such evaporative polydialkylsiloxanes is that when they are applied to hair, they do not leave behind a greasy residue. As used herein in relation to the polyalkylsiloxane, "evaporative" means having a significant vapor pressure under ambient conditions, which can be classified further as volatile or near volatile. Volatile as used herein is a vapor pressure of at least 0.8 mmHg, preferably at least 2 mmHg at 25° C. and near-volatile is having a vapor pressure of about 0.01 to about 0.14 mmHg, more preferably from about 0.01 to about 0.10 mmHg, and most preferably from about 0.01 to about 0.05. Vapor pressure can be measured according to methods commonly used in the art.

Examples of suitable polydialkylsiloxanes are hexylmethicone sold by Clariant Corporation under the product name SILCARE™ 41M10 (CAS #1873-90-1), caprylylmethicone sold by Clariant Corporation under the product name SILCARE™ 41M15 (CAS #17955-88-3), stearoxytrimethylsilane sold by Clariant Corporation under the product name SILCARE™ 1M71 (CAS #18748-98-6), octylmethicone sold under the product name SILSOST™ 034 (Crompton and Knowles), hexylmethicone sold as DC2-1731 (Dow-Corning), and octylmethicone sold as DC2-1732 (Dow-Corning).

The compositions according to the present invention can be formulated into, for example, shampoos, conditioners, hair treatment creams, styling gels, hair mousse, pump hair sprays, aerosol hair sprays, set lotions, blow styling lotions, hair color lotions, hair relaxing compositions, permanent wave first agents, permanent wave second agents, and permanent color.

The compositions of the present invention can be formulated into or with any cosmetically acceptable carrier or diluent. Examples of such carriers or diluents are water, alcohols, polyols, and oils such as, for example, hydrocarbon oils and silicone oils. The carrier or diluent may be present in amounts of 0% to about 90%, by weight with respect to the total weight of the composition, which is inclusive of numerals and fractions thereof with this range including 5%, 10%, 15%, 20%, 25%, 30%, 35%, 40%, 45%, 50%, 55%, 60%, 65%, 70%, 75%, 80%, and 85%.

The compositions of the present invention may further comprise one or more components known for use in hair care compositions. These components can be present in an amount of from about 0 to about 90% by weight with respect to the total weight of the composition, which is inclusive of numerals and fractions thereof with this range including 0.01%, 0.1%, 0.5%, 1%, 5%, 10%, 15%, 20%, 25%, 30%, 35%, 40%, 45%, 50%, 55%, 60%, 65%, 70%, 75%, 80%, 85% and 90%.

Examples of such components include surfactants that are suitable for use on the hair or the skin. Suitable surfactants include anionic surfactants, nonionic surfactants, amphoteric surfactants, zwitterionic surfactants, or mixtures thereof. Surfactants useful in the invention include those described in Kirk-Othmer, Encyclopedia of Chemical Technology (4$^{th}$ Ed.), vol. 23, John Wiley and Sons, Inc., NY and International Cosmetic Ingredient Dictionary and Handbook (8$^{th}$ Ed.) vol. 1–3 (2000), The Cosmetic, Toiletry and Fragrance Association, Washington, D.C. The surfactant can be selected for its cleansing property, foaming property, lathering property, emulsifying property or other desirable property.

Other examples include, but are not limited to, ultraviolet light filters, dyes, hair colorants, hair fixatives, hair waving agents, hair straightening agents, organic solvents or diluents, foam boosters, pH adjusting agents, conditioning agents, humectants, lipids, fragrances, preservatives, proteins, protein derivatives, amino acids, amino acid derivatives, skin active agents, suspending agents, sunscreens, thickeners, vitamins, ceramide, uv absorbers (e.g., benzophenone), botanicals, anti-oxidants, retinoid, anti-dandruff, anti hair-loss and viscosity adjusting agents. These and other cosmetic additives commonly used in hair care formulations are described in, for example, International Cosmetic Ingredient Dictionary and Handbook (7$^{th}$ Ed.) vol. 1–3 (1997), The Cosmetic, Toiletry and Fragrance Association, Washington, D.C.

The compositions of the present invention can be prepared by using various formulation and mixing methods commonly employed in the art to prepare hair care compositions, such as shampoos, conditioners, leave-in-treatments and/or hair coloring agents.

The compositions of the present invention are used by applying to the hair before, during or after the hair has been colored or dyed. The hair may be wet, dry or semi-dry. In the case where the polydialkylsiloxanes are provided in a shampoo or conditioner, the composition may be used in a conventional manner for cleansing and conditioning the hair.

The compositions described herein can be applied to the hair by working, rubbing, or massaging the composition into the hair so that substantially all or some of the hair is contacted with the composition. In one embodiment where treatment for only a portion of the hair is needed, the composition can be applied to the localized region as needed.

According to one embodiment of the present invention, a method of reducing color loss in hair comprising applying the hair care composition set forth above to the hair in an amount effective to reduce color loss in the hair is provided. Preferably, the method is practiced on hair which is need of reduction of color loss.

"Reducing color loss" as used herein means a reduction in color loss in hair relative to hair not treated with the compositions described herein. Color retention or color loss is within the skill of the art and can be measured using a chromometer, which is a procedure commonly used in the art to measure color intensity of the hair (for example, Berthuaume et al (1995), J. Soc. Cosmet. Chem. 46:231–245). The hair is measured at one or more of the root, the middle, and the end of a hair prior to treatment, serve as the baseline measurement. Next, the hair care composition is applied to half of the hair sample, e.g., half a head of hair, while the other half is not treated. Then the entire hair sample, e.g., head, is shampooed and conditioned. Once dried, the chromometer measurement is repeated. By subtracting the end result from the baseline, a change in color intensity can be determined.

The inventors have also surprisingly discovered that application of the compositions set forth above provides an increased volume to the hair, for example head hair, when applied thereon. Accordingly, one embodiment of the present invention is directed to methods of providing volume to the hair ("volumizing") comprising applying the hair care composition set forth above to the hair in an amount effective to volumize the hair. Preferably, the method is practiced on hair which is in need of volumization.

An increase in hair volume or volumizing the hair is determined as any visual increase in hair volume as assessed by the following method. A part of a hair sample is treated with the polydialkylsiloxane, and another part is not so treated. The treated portion of the hair is compared to the untreated hair for any visual increase in hair volume.

In another embodiment, the present invention provides methods of reducing the effects of oxidation on the hair, such oxidation typically caused by the ultraviolet rays of the sun or by use of shampoos. The reduction in oxidation can be effectuated by applying the polydialkylsiloxane together with or separately from one or more ultraviolet light filters, UV absorbers and the like, which can be present in an amount to prevent damage to hair by UV light. Such amounts include, for example, from about 0.01% to about 1%, which is inclusive of 0.05%, 0.1%, 0.2%, 0.3%, 0.4%, 0.5%, 0.6%, 0.7%, 0.8%, 0.9% and 0.95%.

A review of physical blockers may be found at "Sun Protection Effect of Nonorganic Materials," by S. Nakada & H. Konishi, *Fragrance Journal*, Volume 15, pages 64–70 (1987), which is incorporated by reference herein.

It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

The sunscreens which may be included in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517, 104, EP-0,570,838, EP-0,796,851, EP-0,775,698, EP-0,878, 469, EP-0,933,376, EP-0,893,119, EP-0,669,323, GB-2,303, 549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Sunscreens active in the UV-A and/or UV-B range can also include:
  p-aminobenzoic acid,
  oxyethylene (25 mol) p-aminobenzoate,
  2-ethylhexyl p-dimethylaminobenzoate,
  ethyl N-oxypropylene p-aminobenzoate,
  glycerol p-aminobenzoate,
  4-isopropylbenzyl salicylate,
  2-ethylhexyl 4-methoxycinnamate,
  methyl diisopropylcinnamate,
  isoamyl 4-methoxycinnamate,
  diethanolamine 4-methoxycinnamate,
  3-(4'-trimethylammunium)-benzyliden-bornan-2-one methylsulfate,
  2-hydroxy-4-methoxybenzophenone,
  2-hydroxy-4-methoxybenzophenone-5-sulfonate,
  2,4-dihydroxybenzophenone,
  2,2',4,4'-tetrahydroxybenzophenone,
  2,2'-dihydroxy-4,4'dimethoxybenzophenone,
  2-hydroxy-4-n-octoxybenzophenone,
  2-hydroxy-4-methoxy-4'-methoxybenzophenone,
  -(2-oxoborn-3-ylidene)-tolyl-4-sulfonic acid and soluble salts thereof,
  3-(4'-sulfo)benzyliden-bornan-2-one and soluble salts thereof,
  3-(4'methylbenzylidene)-d,l-camphor,
  3-benzylidene-d,l-camphor,
  benzene 1,4-di(3-methylidene-10-camphosulfonic) acid and salts thereof (the product Mexoryl SX described in U.S. Pat. No. 4,585,597 issued to Lange et al. on Apr. 29, 1986),
  urocanic acid,
  2,4,6-tris[p-(2'-ethylhexyl-1'-oxycarbonyl)-anilino]-1,3,5-triazine,
  2-[(p-(tertiobutylamido)anilino]-4,6-bis-[(p-(2'-ethylhexyl-1'-oxycarbonyl)anilino]-1,3,5-triazine,
  2,4-bis {[4-(2-ethyl-hexyloxy)]-2-hydroxy]-phenyl}-6-(4-methoxy-phenyl)-1,3,5-triazine ("TINOSORB S" marketed by Ciba),
  the polymer of N-(2 et 4)-[(2-oxoborn-3-yliden)methyl] benzyl]-acrylamide,
  1,4-bisbenzimidazolyl-phenylen-3,3',5,5'-tetrasulfonic acid and salts thereof,
  the benzalmalonate-substituted polyorganosiloxanes,
  the benzotriazole-substituted polyorganosiloxanes (Drometrizole Trisiloxane),
  dispersed 2,2'-methylene-bis-[6-(2H-benzotriazol-2-yl)-4-(1,1,3,3 -tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and
  solubilized 2,2'-methylene-bis-[6-(2H-benzotriazol-2-yl)-4-(methyl)phenol] such as that marketed under the trademark MIXXIM BB/200 by Fairmount Chemical. Typically combinations of one of more of these sunscreens are used.

The dibenzoyl methane derivatives other than avobenzone are described, for example, in FR-2,326,405, FR-2,440,933 and EP-0,114,607, hereby expressly incorporated by reference.

Other dibenzoyl methane sunscreens other than avobenzone include (whether singly or in any combination):

2-methyldibenzoylmethane 4-methyldibenzoylmethane 4-isopropyldibenzoylmethane 4-tert.-butyldibenzoylmethane 2,4-dimethyldibenzoylmethane 2,5-dimethyldibenzoylmethane 4,4'-diisopropyldibenzoylmethane 4,4'-dimethoxydibenzoylmethane 2-methyl-5-isopropyl-4'-methoxydibenzoylmethane 2-methyl-5-tert-butyl-4'-methoxydibenzoylmethane 2,4-dimethyl-4'-methoxydibenzoylmethane 2,6-dimethyl-4-tert.-butyl-4'-methoxydibenzoylmethane Additional ultraviolet light filters or sunscreen agents that can be used include, but are not limited to, those described in pages 1788 to 1789 of the International Cosmetic, Toiletries, and Fragrance Association Handbook, 8$^{th}$ Edition (2000).

The present invention also provides kits or prepackaged materials containing the compositions of the present invention. These kits or prepackaged materials can provide the polydialkylsiloxanes mixed directly into a hair coloring composition, provided separately, but in the same package as the hair coloring compositions, which then can be premixed and applied to the hair; or applied sequentially. Likewise, the polydialkylsiloxanes can be provided prepackaged kit coupled to one or more hair treatment compositions (e.g., shampoos, conditioners, and others as described herein and known in the art).

In another embodiment, the polydialkylsiloxanes s of the present invention can be added onto or impregnated into a non-woven, woven, sponge, and/or sponge-like substrate for delivery to the user. Such articles may consist of one or more layers, which layers may be apertured or non-apertured and the polydialkylsiloxanes can be provided mixed in a topical or cosmetic composition or may be added separately from other active or cosmetically effective agents to provide a hair color retention benefit to the user.

The following Examples provide an illustration of embodiments of the invention and should not be construed to limit the scope of the invention, which is set forth in the appended claims. In the following Examples, all methods described are conventional unless otherwise specified.

EXAMPLES

A total of 7 panelists with freshly colored hair were shampooed, conditioned, and then evaluated with a chromometer and compared to the chromometer values of untreated hair (ΔL values, where the higher the number, the greater the color loss). Hair stylists applied the treatment, which was a 90/10 blend of hexyl methicones/ethanol to test zones on the panelist. These test zones were compared to shampoo and rinse-off conditioner controls. After 9 cycles the results were as follows:

| | Stylist applied color and then treated hair | |
|---|---|---|
| Panelist[1] | ΔL after 4 cycles[2] | ΔL after 9 cycles[2] |
| 1 (MC)-Test | 1.6 | *1.8* |
| Control | 1.9 | *3.2* |
| 2 (PKn)-Test | 1.4 | *1.4* |
| Control | 1.7 | *2.7* |
| 3 (EK)-Test | *0.9* | *1.6* |
| Control | *2.1* | *3.6* |
| 4 (EP)-Test | 2.4 | 2.7 |
| Control | 2.7 | 3.5 |

[1]The initial L value for panelists 1–3 was approximately 20 and the L value for panelist 4 was 25.
[2]Those values in bold and italic font indicate an visual difference between the test and control zones.

Interestingly, a significantly greater color loss was observed on those consumers who self-applied color compared to the stylist-applied coloring products. In conjunction with the higher rates of color loss, the benefit observed was almost immediate.

Panelists self-applied color within 1 week prior to test followed by Stylist treatment

| Panelist | ΔL after 4 cycles[1] | ΔL after 7 cycles[1] |
|---|---|---|
| 1 (KR)-Test | *2.2* | *4.8* |
| Control | *6.0* | *8.6* |
| 2 (LA)-Test | *2.0* | *3.9* |
| Control | *3.4* | *5.7* |
| 3 (PKa)-Test | *4.2* | *5.0* |
| Control | *6.8* | *8.8* |

[1]visual differences observed between test and control zones

As illustrated in the tables, both expert and novice graders noticed a color-loss reduction when the difference between the two products was greater than 1.3 units. Therefore, Hexyl Methicone provides a noticeable, meaningful, benefit.

In addition to the color protection effect, trained stylists observed a volumizing effect on the hair applied with hexyl methicones. The fullness of the hair was judged visually on a scale of 1 (very limp) to 5 (very full). On a half-head test, the side with the applied hexyl methicones was rated on the average of 3.6 while the control side was rated as 2.2.

Obviously, numerous modifications and variations on the present invention are possible in light of the above teachings. It is therefore to be understood that within the scope of the appended claims, the invention may be practiced otherwise than as specifically described herein.

What is claimed is:

1. A method of reducing color loss in hair comprising applying at least one polydialkylsiloxane having at least one pendant alkyl moiety, said polydialkylsiloxane having a vapor pressure vapor pressure of at least 0.8 mmHg. at 25° C., to the hair in an amount effective to reduce color loss in the hair.

2. A method of protecting hair from the effects of oxidation comprising applying at least one polydialkylsiloxane having at least one pendant alkyl moiety, said polydialkylsiloxane having a vapor pressure vapor pressure of at least 0.8 mmHg. at 25° C., to the hair in an amount effective to protect the hair from the effects of oxidation.

3. A method of reducing color loss in dyed hair comprising applying at least one polydialkylsiloxane having at least one pendant alkyl moiety, said polydialkylsiloxane having a vapor pressure vapor pressure of at least 0.8 mmHg. at 25° C., to the hair in an amount effective to reduce color loss in the hair.

4. The method of claim 1, wherein said polydialkylsiloxane is present in a composition.

5. The method of claim 4, wherein said composition comprises at least two polydialkylsiloxanes, each having at least one pendant alkyl moiety.

6. The method of claim 4, wherein said polydialkylsiloxane is an alkyl methicone.

7. The method of claim 6, wherein said alkyl methicone is selected from the group consisting of substituted alkane methicone, unsubstituted alkane methicone, substituted alkene methicone, unsubstituted alkene methicone, substituted alkyne methicone, unsubstituted alkyne methicone, substituted aryl methicone, unsubstituted aryl methicones, and mixtures thereof.

8. The method of claim 7, wherein said alkyl methicone is a substituted alkane methicone or an unsubstituted alkane methicone.

9. The method of claim 6, wherein said alkyl methicone is a $C_5$ to $C_{16}$ alkyl methicone.

10. The method of claim 6, wherein said alkyl methicone is a $C_5$ to $C_{10}$ alkyl methicone.

11. The method of claim 6, wherein said alkyl methicone is a $C_6$ alkyl methicone.

12. The method of claim 4, wherein said composition comprises at least 20% of said polydialkylsiloxane.

13. The method of claim 4, wherein said polydialkylsiloxane is a compound of the structure:

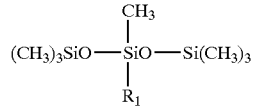

wherein $R_1$ is an alkyl moiety with 1 to 50 carbon atoms.

14. The method of claim 13, wherein $R_1$ is an alkyl moiety with 2 to 30 carbon atoms.

15. The method of claim 13, wherein $R_1$ is an alkyl moiety with 3 to 20 carbon atoms.

16. The method of claim 13, wherein $R_1$ is an alkyl moiety with 4 to 16 carbon atoms.

17. The method of claim 13, wherein $R_1$ is an alkyl moiety with 5 to 10 carbon atoms.

18. The method of claim 4, wherein said polydialkylsiloxane is a compound of the structure:

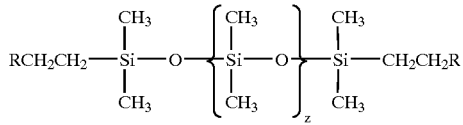

wherein R is hydrogen or an $C_1$ to $C_{15}$ alkyl group and z is 1 to 5.

19. The method of claim 18, wherein R is hydrogen.

20. The method of claim 18, wherein z is 1.

21. The method of claim 18, wherein the molecular weight of the compound is from about 300 to 600.

22. The method of claim 18, wherein the hydrocarbon-to-silicone ratio in the compound is from about 0.25 to about 1.00.

23. The method of claim 4, wherein said composition comprises at least 30% of said polydialkylsiloxane.

24. The method of claim 4, wherein the composition further comprises water.

25. The method of claim 4, wherein the composition further comprises at least one alcohol.

26. The method of claim 4, wherein the composition further comprises at least one polyol.

27. The method of claim 4, wherein the composition further comprises at least one oil.

28. The method of claim 27, wherein said oil is a hydrocarbon oil.

29. The method of claim 27, wherein said oil is a silicone oil.

30. The method of claim 4, wherein the composition is in the form an emulsion, gel, dispersion, paste, cream, aerosol or liquid.

31. The method of claim 4, wherein the composition is a conditioner.

32. The method of claim 4, wherein the composition is a shampoo.

33. The method of claim 4, wherein the composition is a hair mouse.

34. The method of claim 4, the composition is a detangler.

35. The method of claim 4, wherein the composition further comprises a hair colorant.

36. The method of claim 4, wherein the composition further comprises one or more ingredients selected from the group consisting of a surfactant, a ultraviolet light filter, a dye, an organic solvent, an organic diluents, a foam booster, a pH adjusting agent, a conditioning agent, a humectant, a lipid, a fragrance, a preservative, a protein, a skin active agent, a suspending agent, a sunscreen, a thickener, a vitamin, a ceramide, a uv absorber, a botanical, an anti-oxidant, a retinoid, an anti-dandruff agent, an anti hair-loss agent, and a viscosity adjusting agents.

37. The method of claim 4, wherein the composition further comprises a uv absorber.

38. The method of claim 37, wherein the uv absorber is a benzophenone.

39. The method of claim 4, wherein said polydialkylsiloxane is unsubstituted.

40. The method of claim 2, wherein said polydialkylsiloxane is present in a composition.

41. The method of claim 40, wherein said composition comprises at least two polydialkylsiloxanes, each having at least one pendant alkyl moiety.

42. The method of claim 40, wherein said polydialkylsiloxane is an alkyl methicone.

43. The method of claim 42, wherein said alkyl methicone is selected from the group consisting of substituted alkane methicone, unsubstituted alkane methicone, substituted alkene methicone, unsubstituted alkene methicone, substituted alkyne methicone, unsubstituted alkyne methicone, substituted aryl methicone, unsubstituted aryl methicones, and mixtures thereof.

44. The method of claim 43, wherein said alkyl methicone is a substituted alkane methicone or an unsubstituted alkane methicone.

45. The method of claim 42, wherein said alkyl methicone is a $C_5$ to $C_{16}$ alkyl methicone.

46. The method of claim 42, wherein said alkyl methicone is a $C_5$ to $C_{10}$ alkyl methicone.

47. The method of claim 42, wherein said alkyl methicone is a $C_6$ alkyl methicone.

48. The method of claim 40, wherein said composition comprises at least 20% of said polydialkylsiloxane.

49. The method of claim 40, wherein said polydialkylsiloxane is a compound of the structure:

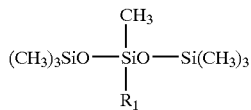

wherein $R_1$ is an alkyl moiety with 1 to 50 carbon atoms.

50. The method of claim 49, wherein $R_1$ is an alkyl moiety with 2 to 30 carbon atoms.

51. The method of claim 49, wherein $R_1$ is an alkyl moiety with 3 to 20 carbon atoms.

52. The method of claim 49, wherein $R_1$ is an alkyl moiety with 4 to 16 carbon atoms.

53. The method of claim 49, wherein $R_1$ is an alkyl moiety with 5 to 10 carbon atoms.

54. The method of claim 40, wherein said polydialkylsiloxane is a compound of the structure:

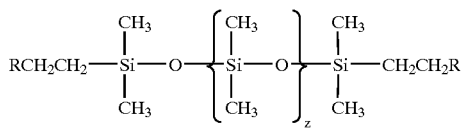

wherein R is hydrogen or an $C_1$ to $C_{15}$ alkyl group and z is 1 to 5.

55. The method of claim 54, wherein R is hydrogen.

56. The method of claim 54, wherein z is 1.

57. The method of claim 54, wherein the molecular weight of the compound is from about 300 to 600.

58. The method of claim 54, wherein the hydrocarbon-to-silicone ratio in the compound is from about 0.25 to about 1.00.

59. The method of claim 40, wherein said composition comprises at least 30% of said polydialkylsiloxane.

60. The method of claim 40, wherein the composition further comprises water.

61. The method of claim 40, wherein the composition further comprises at least one alcohol.

62. The method of claim 40, wherein the composition further comprises at least one polyol.

63. The method of claim 40, wherein the composition further comprises at least one oil.

64. The method of claim 63, wherein said oil is a hydrocarbon oil.

65. The method of claim 63, wherein said oil is a silicone oil.

66. The method of claim 40, wherein the composition is in the form an emulsion, gel, dispersion, paste, cream, aerosol or liquid.

67. The method of claim 40, wherein the composition is a conditioner.

68. The method of claim 40, wherein the composition is a shampoo.

69. The method of claim 40, wherein the composition is a hair mouse.

70. The method of claim 40, wherein the composition is a detangler.

71. The method of claim 40, wherein the composition further comprises a hair colorant.

72. The method of claim 40, wherein the composition further comprises one or more ingredients selected from the group consisting of a surfactant, a ultraviolet light filter, a dye, an organic solvent, an organic diluents, a foam booster, a pH adjusting agent, a conditioning agent, a humectant, a lipid, a fragrance, a preservative, a protein, a skin active agent, a suspending agent, a sunscreen, a thickener, a vitamin, a ceramide, a uv absorber, a botanical, an anti-oxidant, a retinoid, an anti-dandruff agent, an anti hair-loss agent, and a viscosity adjusting agents.

73. The method of claim 40, wherein the composition further comprises a uv absorber.

74. The method of claim 40, wherein the uv absorber is a benzophenone.

75. The method of claim 40, wherein said polydialkylsiloxane is unsubstituted.

76. The method of claim 3, wherein said polydialkylsiloxane is present in a composition.

77. The method of claim 76, wherein said composition comprises at least two polydialkylsiloxanes, each having at one pendant alkyl moiety.

78. The method of claim 76, wherein said polydialkylsiloxane is an alkyl methicone.

79. The method of claim 78, wherein said alkyl methicone is selected from the group consisting of substituted alkane methicone, unsubstituted alkane methicone, substituted alkene methicone, unsubstituted alkene methicone, substituted alkyne methicone, unsubstituted alkyne methicone, substituted aryl methicone, unsubstituted aryl methicones, and mixtures thereof.

80. The method of claim 79, wherein said alkyl methicone is a substituted alkane methicone or an unsubstituted alkane methicone.

81. The method of claim 78, wherein said alkyl methicone is a $C_5$ to $C_{16}$ alkyl methicone.

82. The method of claim 78, wherein said alkyl methicone is a $C_5$ to $C_{10}$ alkyl methicone.

83. The method of claim 78, wherein said alkyl methicone is a $C_6$ alkyl methicone.

84. The method of claim 76, wherein said composition comprises at least 20% of said polydialkylsiloxane.

85. The method of claim 76, wherein said polydialkylsiloxane is a compound of the structure:

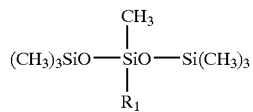

wherein $R_1$ is an alkyl moiety with 1 to 50 carbon atoms.

86. The method of claim 85, wherein $R_1$ is an alkyl moiety with 2 to 30 carbon atoms.

87. The method of claim 85, wherein $R_1$ is an alkyl moiety with 3 to 20 carbon atoms.

88. The method of claim 85, wherein $R_1$ is an alkyl moiety with 4 to 16 carbon atoms.

89. The method of claim 85, wherein $R_1$ is an alkyl moiety with 5 to 10 carbon atoms.

90. The method of claim 76, wherein said polydialkylsiloxane is a compound of the structure:

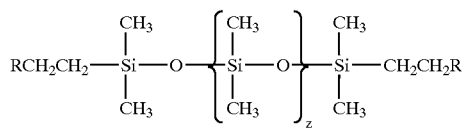

wherein R is hydrogen or an $C_1$ to $C_{15}$ alkyl group and z is 1 to 5.

91. The method of claim 90, wherein R is hydrogen.

92. The method of claim 90, wherein z is 1.

93. The method of claim 90, wherein the molecular weight of the compound is from about 300 to 600.

94. The method of claim 90, wherein the hydrocarbon-to-silicone ratio in the compound is from about 0.25 to about 1.00.

95. The method of claim 76, wherein said composition comprises at least 30% of said polydialkylsiloxane.

96. The method of claim 76, wherein the composition further comprises water.

97. The method of claim 76, wherein the composition further comprises at least one alcohol.

98. The method of claim 76, wherein the composition further comprises at least one polyol.

99. The method of claim 76, wherein the composition further comprises at least one oil.

100. The method of claim 99, wherein said oil is a hydrocarbon oil.

101. The method of claim 99, wherein said oil is a silicone oil.

102. The method of claim 76, wherein the composition is in the form an emulsion, gel, dispersion, paste, cream, aerosol or liquid.

103. The method of claim 76, wherein the composition is a conditioner.

104. The method of claim 76, wherein the composition is a shampoo.

105. The method of claim 76, wherein the composition is a hair mouse.

106. The method of claim 76, wherein the composition is a detangler.

107. The method of claim 76, wherein the composition further comprises a hair colorant.

108. The method of claim 76, wherein the composition further comprises one or more ingredients selected from the group consisting of a surfactant, a ultraviolet light filter, a dye, an organic solvent, an organic diluents, a foam booster, a pH adjusting agent, a conditioning agent, a humectant, a lipid, a fragrance, a preservative, a protein, a skin active agent, a suspending agent, a sunscreen, a thickener, a vitamin, a ceramide, a uv absorber, a botanical, an anti-oxidant, a retinoid, an anti-dandruff agent, an anti hair-loss agent, and a viscosity adjusting agents.

109. The method of claim 76, wherein the composition further comprises a uv absorber.

110. The method of claim 109, wherein the uv absorber is a benzophenone.

111. The method of claim 76, wherein said polydialkylsiloxane is unsubstituted.

* * * * *